Figure 1:
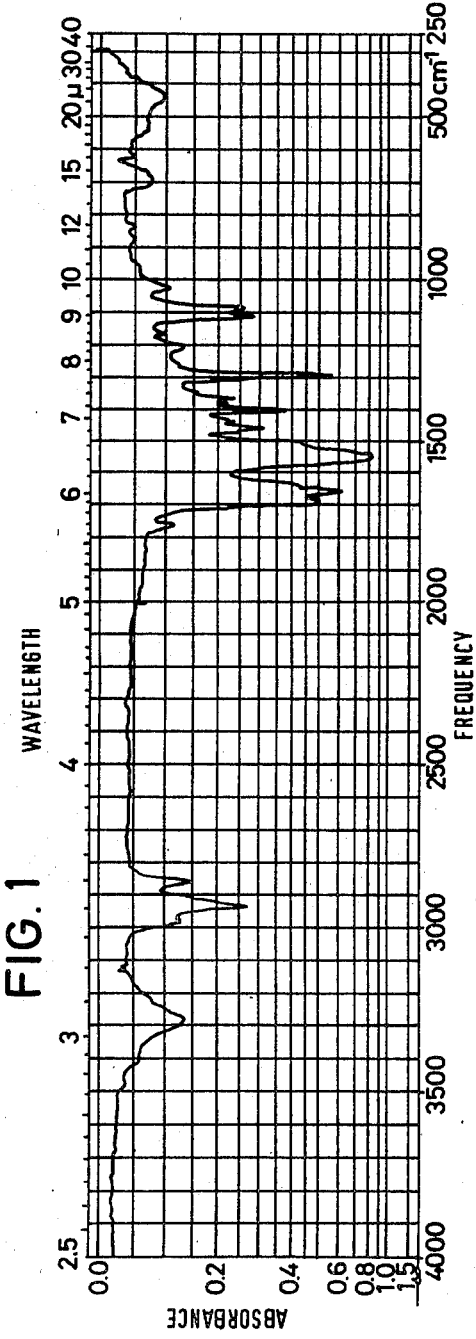

United States Patent [19]

Dalibor

[11] 4,332,965
[45] Jun. 1, 1982

[54] BLOCKED POLYISOCYANATES FORMED FROM A POLYISOCYANATE CONTAINING BIURET GROUPS AND FROM AN ACETOACETIC ACID ALKYL ESTER

[75] Inventor: Horst Dalibor, Norderstedt, Fed. Rep. of Germany

[73] Assignee: Hoechst Aktiengesellschaft, Frankfurt am Main, Fed. Rep. of Germany

[21] Appl. No.: 126,443

[22] Filed: Mar. 3, 1980

Related U.S. Application Data

[63] Continuation of Ser. No. 779,156, Mar. 18, 1977, abandoned.

[30] Foreign Application Priority Data

Mar. 25, 1976 [DE] Fed. Rep. of Germany ....... 2612783

[51] Int. Cl.³ ............................................. C07C 103/87
[52] U.S. Cl. ....................................... 560/169; 528/45
[58] Field of Search ........................................ 560/169

[56] References Cited

U.S. PATENT DOCUMENTS

| | | | |
|---|---|---|---|
| 3,201,372 | 8/1965 | Wagner | 260/77.5 |
| 3,454,621 | 7/1969 | Engel | 560/25 |
| 3,746,689 | 7/1973 | Narayan | 560/169 |

FOREIGN PATENT DOCUMENTS

| | | |
|---|---|---|
| 96601 | 3/1973 | German Democratic Rep. |
| 1412882 | 11/1975 | United Kingdom. |

OTHER PUBLICATIONS

Houben–Weyl, "Method der Organischen Chemie", vol. 14/2, pp. 61–70.

*Primary Examiner*—Michael L. Shippen
*Attorney, Agent, or Firm*—Gordon W. Hueschen

[57] ABSTRACT

The invention relates to polyisocyanates which are blocked with an acetoacetic acid alkyl ester.

1 Claim, 9 Drawing Figures

BLOCKED POLYISOCYANATES FORMED FROM A POLYISOCYANATE CONTAINING BIURET GROUPS AND FROM AN ACETOACETIC ACID ALKYL ESTER

This application is a continuation of our prior-filed application Ser. No. 779,156 filed Mar. 18, 1977, now abandoned.

BACKGROUND OF THE INVENTION

The manufacture of blocked or masked polyisocyanates is known and is described in Houben-Weyl "Methoden der Organischen Chemie" ("Methods of Organic Chemistry"), volume 14/2, pages 61–70.

Reaction products of hexamethylene-1,6-diisocyanate with tert.-butanol, phenol, acetoacetic acid ethyl ester, malonic acid ester, acetylacetone, phthalimide, imidazole, hydrogen chloride, hydrogen cyanide and caprolactam are known.

This aliphatic diisocyanate was reacted with compounds which are split off again at elevated temperature to liberate the isocyanate group. Products of this type are designated isocyanate donors or "moderators". In contrast with the free diisocyanates, masked diisocyanates of this type make it possible to manufacture mixtures with substances or solvents which contain hydroxyl groups, without a reaction taking place in the course thereof. It is therefore possible, by means of masked polyisocyanates, to manufacture mixtures with products which contain hydroxyl groups, such as higher molecular polyesters or polyethers, and which are stable on storage and only give the desired isocyanate reactions at an elevated temperature. They are of great importance both for the manufacture of rubber-elastic products via storable intermediate stages and for the manufacture of wire lacquers, and in the textile field. The donor effect comes about because virtually all adducts which are formed from isocyanates at a moderately elevated temperature redissociate once more at higher temperatures, equilibria being set up. The establishment of these equilibria is accelerated by adding tertiary bases.

In combination with polymers containing hydroxyl groups, many of these masked polyisocyanates exhibit an unsatisfactory crosslinking at low stoving temperatures. Other masked polyisocyanates which redissociate at lower temperatures produce scission products which must not be employed for stoving lacquerings because of their toxicity.

A known adduct, manufactured from hexamethylene diisocyanate and acetoacetic acid ethyl ester, produces two scission products, namely acetoacetic acid ethyl ester, which is less toxic, and hexamethylene diisocyanate, which is not physiologically harmless. This toxic effect is further increased because the hexamethylene diisocyanate is only liberated above 140° C. The known adduct has a melting point of 81°–82° C. and must therefore be manufactured in the melt above the melting point temperature, that is to say at about 90° C., as a result of which an undesirable yellow coloration takes place which can only be removed by recrystallisation. This solid adduct has a tendency to crystallise and leads to an undesirable inhomogeneity in the manufactured lacquer solutions. Thus, for example, stoved lacquers with greatly impaired film properties are produced by the combination of polymers containing hydroxyl groups and the known adduct.

It is an object of the invention to provide completely or partially blocked polyisocyanates which are present, at room temperature and also at temperatures of about 0° C., as solutions in inert solvents which are customary in the lacquer industry.

It is a further object of this invention to provide completely or partially blocked polyisocyanates which, when completely blocked, produce, in the temperature range from 80° to 130° C., preferably 90° to 110° C., crosslinked reaction products in the presence of polymers containing hydroxyl groups. In addition, the physiological behaviour of the blocked polyisocyanates, also after their redissociation into the starting components, should be less harmful than that of the known blocked and free polyisocyanates.

SUMMARY

The invention relates to polyisocyanates which are blocked with an acetoacetic acid alkyl ester and which have the following formula (I)

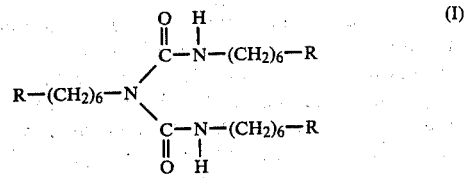

wherein R denotes the radical

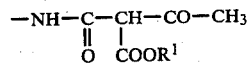

and one to three units of it are present in the compound and wherein, in the case where one or two units of R having this meaning are present, the remaining radical R denotes the radical —NCO, and wherein $R^1$ denotes, individually or as a mixture, the methyl, ethyl, propyl, n-butyl, tert.-butyl, isobutyl, sec.-butyl, pentyl, hexyl, heptyl, octyl, nonyl, decyl and dodecyl radicals.

In the manufacture of the mono-masked compounds having the formula (I a)

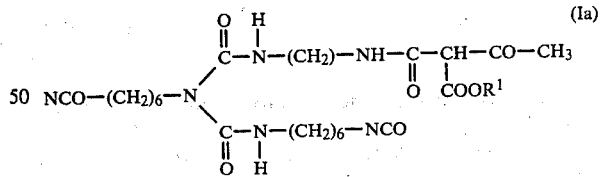

the necessary starting components are reacted in the presence of an inert solvent which consists of aromatic hydrocarbons and/or organic esters having boiling points of 70° to 170° C. In the course thereof, 1 mol of the triisocyanate having the formula (II)

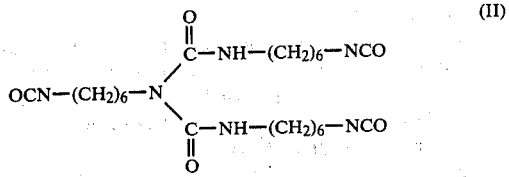

is reacted with 1 mol of an acetoacetic acid alkyl ester of the type already mentioned, and it is preferable to employ the acetoacetic acid alkyl ester in an excess of 0.05 to 0.1 mol.

In the manufacture of the di-masked compounds having the formula (I b)

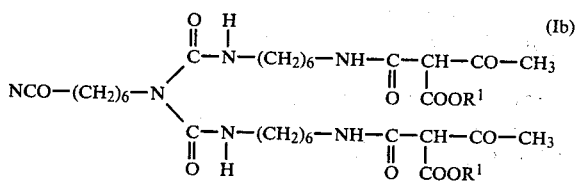

the necessary starting components are also reacted in the presence of the inert solvents already mentioned at the temperatures already mentioned. Here, however, in contrast, 1 mol of the triisocyanate of the formula (II) is reacted with 2 mols of acetoacetic acid alkyl ester of the type already mentioned, and it is preferable to employ the acetoacetic acid alkyl ester in an excess of 0.05 to 0.1 mol.

A variant in the manufacture of the di-masked compounds having the formula (I b) wherein $R^1$ represents two different alkyl radicals, consists in first manufacturing a mono-masked product having the formula (I a) by reacting one mol of the triisocyanate having the formula (II) with 1 mol of an acetoacetic acid alkyl ester and reacting this mono-masked product with a further mol of another acetoacetic acid alkyl ester.

The reaction of the triisocyanate having the formula (II) with acetoacetic acid ethyl ester in the first stage to give a product having the formula (I a) and the reaction of the resulting product with acetoacetic acid tert.-butyl ester may be mentioned as an example. Amongst the masked groups in a product with mixed masking which has been manufactured in this way, the tert.-butyl radical is particularly reactive and can therefore be split off at a lower temperature compared with the ethyl radical.

The completely masked products having the formula (I c)

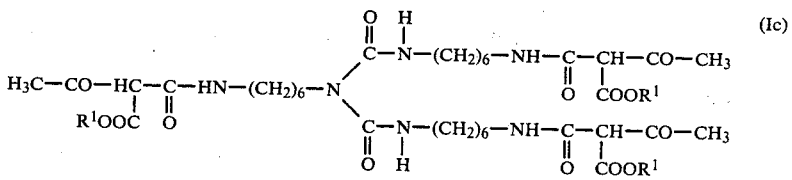

wherein $R^1$ denotes, individually or as a mixture, the methyl, ethyl, propyl, isopropyl, n-butyl, tert.-butyl, isobutyl, sec.-butyl, pentyl, hexyl, heptyl, octyl, nonyl, decyl and dodecyl radicals, are manufactured by reacting one mol of triisocyanate of the formula (II) with 3 to 3.3 mols of an acetoacetic acid alkyl ester.

They can, however, also be manufactured by reacting a mono-masked product having the formula (I a) with 2 to 2.2 mols of an acetoacetic acid alkyl ester. It is also possible, however, to react the di-masked products having the formula (I b) with 1 to 1.1 mols of an acetoacetic acid alkyl ester.

As the preceding embodiments show, it is thus possible to manufacture products having the formula (I c) in which two or three units of $R^1$ are identical or in which each $R^1$ represents a different alkyl radical.

The pentyl radical $C_5H_{11}$ of acetoacetic acid pentyl ester, can be present in 8 isomeric forms (neglecting optical antipodes), as individuals or as a mixture. The starting product, pentanol, for the manufacture of the acetoacetic acid pentyl ester which is reacted with the polyisocyanate, can, for example, be a commercially available fusel oil or a fermentation amyl alcohol, 1-pentanol (n-amyl alcohol or n-butylcarbinol) $H_3C—(CH_2)_3—CH_2OH$; 2-pentanol (sec. amyl alcohol or methylpropylcarbinol), $CH_3—(CH_2)_2—CHOH—CH_3$; 3-pentanol (diethylcarbinol), $CH_3—CH_2—CHOH—CH_2—CH_3$; primary or secondary isoamyl alcohols (3-methyl-1-butanol or 3-methyl-2-butanol respectively), $(CH_3)_2CH—CH_2—CH_2OH$ or $(CH_3)_2CH—CHOH—CH_3$ respectively; or 2-methyl-1-butanol, 2,2-dimethyl-1-propanol or tert.-amyl alcohol (2-methyl-2-butanol). In addition of the 1-hexyl radical, the hexyl radical also exists in 16-isomeric forms. The corresponding hexanols which can be used for the manufacture of acetoacetic acid hexyl ester are described in BEILSTEIN E III, 1: 1,650, and those which exist in the liquid state at room temperature are preferred. The corresponding heptyl alcohols, together with their isomers, which can be used for the manufacture of acetoacetic acid heptyl ester are described in BEILSTEIN E III, 1: 1,679–1,687, and those which exist in the liquid state at room temperature are preferred. The corresponding octyl alcohols, together with their isomers, which can be used for the manufacture of acetoacetic acid octyl ester are described in BEILSTEIN E IV, 1: 1,756, 1,770 and 1,779, and those which exist in the liquid state at room temperature are preferred. The corresponding nonyl alcohols, together with their isomers, which can be used for the manufacture of acetoacetic acid nonyl ester are described in BEILSTEIN E IV, 1: 1,798, 1,803 and 1,804, and those which exist in the liquid state at room temperature are preferred. The corresponding decyl alcohols, together with their isomers, which can be used for the manufacture of acetoacetic acid decyl ester are described in BEILSTEIN E III, 1: 1,758, and those which exist in the liquid state at room temperature are preferred. The corresponding dodecyl alcohols, together with their isomers, which can be used for the manufacture of acetoacetic acid dodecyl ester are described in BEILSTEIN III, 1: 1,781, and those which exist in the liquid state at room temperature are preferred.

Partially or completely masked isocyanates in which the radical $R^1$ contains one to five carbon atoms are preferred.

Examples of inert solvents which can be used, individually or as a mixture, are benzene, alkylbenzenes, methyl acetate, ethyl acetate, propyl acetate, butyl acetate, amyl acetate, methylglycol acetate and ethylglycol acetate.

A further subject of the invention is a process for the manufacture of partially or completely blocked triisocyanates of the formula (I)

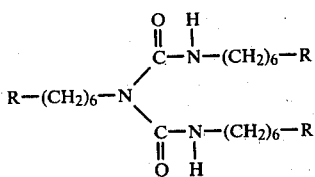

(I)

wherein R denotes the radical

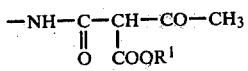

and one to three units of it are present in the compound and wherein, in the case where one or two units of R having this meaning are present, the remaining radical R denotes the radical —NCO and wherein $R^1$ denotes, individually or as a mixture, the methyl, ethyl, propyl, isopropyl, n-butyl, tert.-butyl, isobutyl, sec.-butyl, pentyl, hexyl, heptyl, octyl, nonyl, decyl and dodecyl radicals, characterised in that an acetoacetic acid alkyl ester in which the alkyl radical consists of the methyl, ethyl, propyl, isopropyl, n-butyl, tert.-butyl, isobutyl, sec.-butyl, pentyl, hexyl, heptyl, octyl, nonyl, decyl and dodecyl radicals, is reacted, by heating, in the presence of a catalyst, with a solution of a triisocyanate which contains biuret groups and which has the formula

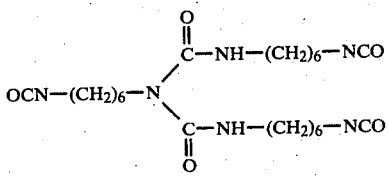

the required quantity of acetoacetic acid alkyl ester being in a slight excess.

A further subject of the invention is the use of the partially or completely blocked diisocyanates of the formula (I) as a crosslinking agent for the manufacture of synthetic resins, plastics or plastic coatings.

The particular advantage of the new, completely masked compounds consists in the fact that they can be manufactured by reaction of the components in the presence of catalysts, in solutions, at fairly low temperatures between approximately 75° C. and 100° C., preferably 75° to 80° C., and the reaction products are still in the form of a solution even at 0° C. In general, the reaction requires 2 to 20 hours.

The partially masked compounds of this invention are highly reactive by virtue of the free isocyanate group.

Zinc acetylacetonate is used as the catalyst, because it gives products which are completely free from turbidity.

In addition, reaction products having the low viscosities desired are obtained by this process. These new compounds are distinguished by quite special technological properties. They do not possess the disadvantages which have been described of the blocked polyisocyanates existing hitherto. Lacquer combinations consisting of copolymers which contain hydroxyl groups and which are based on hydroxyalkyl esters of acrylic or methacrylic acid and esters of acrylic or methacrylic acid crosslink with the new, blocked polyisocyanate at 100° to 130° C. under the conditions of a conversion of masked NCO: OH of 0.5 to 1:1, and produce very resistant lacquerings.

The new, blocked isocyanates of the present invention can be used quite generally for all the purposes in lacquer and plastics chemistry in which blocked triisocyanates have already been used successfully.

The following examples are mentioned of polymers containing polyhydroxyl groups or synthetic resins containing hydroxyl groups, which can be crosslinked under hot conditions with the masked polyisocyanates according to the invention: saturated polyester resins, unsaturated polyester resins, saturated or unsaturated, oil-modified or fatty acid-modified alkyd resins, aminoplast resins, polyurethane resins, polyethers, epoxide resins, cellulose acetobutyrate and copolymers containing hydroxyl groups.

Polyester resins which can be used are those which contain, in a co-condensed form, aliphatic and aromatic dicarboxylic acids having 4 to 12 carbon atoms and polyols having 2 to 10 carbon atoms and 2 to 4 primary or secondary hydroxyl groups. Saturated and unsaturated polyester resins of this type are described in Houben-Weyl "Makromolekulare Stoffe II" ("Macromolecular Materials II"), volume 14/2, pages 4 to 42.

Oil-modified or fatty acid-modified alkyd resins which can be used are those which contain, in a co-condensed form, 10 to 50% by weight of saturated or unsaturated aliphatic fatty aids having 8 to 18 carbon atoms, dicarboxylic acids having 4 to 12 carbon atoms and polyols having 2 to 10 carbon atoms and 2 to 4 primary or secondary hydroxyl groups, and also styrenated and acrylated oil alkyd resins, such as are described in Wagner/Sarx "Lackkunstharze" ("Synthetic Resins for Lacquers"), 5th edition, pages 99 to 123.

Aminoplast resins which can be used are those such as are described in Wagner/Sarx "Lackkunstharze" ("Synthetic Resins for Lacquers"), 5th edition, pages 61 to 80.

Epoxide resins which can be used are those which are obtained by reacting bisphenol A and epichlorohydrin in an alkaline medium. Such resins have epoxide equivalents of 450 to 4,000 and softening points, by Durran's method, of 65° to 155° C. Such epoxide resins are described in Houben-Weyl "Makromolekulare Stoffe II" ("Macromolecular Materials II"), volume 14/2, pages 468 to 475. Epoxide resins such as are described in Wagner/Sarx "Lackkunstharze" ("Synthetic Resins for Lacquers"), 5th edition, pages 174 to 194, can also be used.

Cellulose esters having 1 to 4 carbon atoms in the ester radical which can be employed are those which have a butyryl content of 17 to 55% by weight, an acetyl content of 2 to 40% by weight and a hydroxyl content of 0.5 to 5% by weight. Mixed fatty acid esters of cellulose are described in Houben-Weyl "Makromolekulare Stoffe II" ("Macromolecular Materials II"), volume 14/2, pages 877 to 879. Cellulose derivatives such as are described in Wagner/Sarx "Lackkunstharze" ("Synthetic Resins for Lacquers") 5th edition, pages 267 to 270, can also be used.

Copolymers which can be used are those which contain, in a co-polymerised form, acrylic acid or methacrylic acid esters having 1 to 8 carbon atoms in the alcohol radical, hydroxyalkyl acrylate and/or hydroxyalkyl methacrylates and, if appropriate, also other polymerisable monomers, the products having hydroxyl numbers from 33 to 300. Copolymers containing hydroxyl groups are described in the book by Wagner/-

Sarx "Lackkunstharze" ("Synthetic Resins for Lacquers") 5th edition (1971), pages 195 to 242.

The mixing ratio is 5 to 50% by weight of the reaction products according to the invention, obtained from a polyisocyanate containing biuret groups and acetoacetic acid alkyl esters, and 50 to 95% by weight of synthetic resins containing hydroxyl groups. The mixing ratio includes the further requirement that 0.3 to 1.2 NCO groups are employed as blocked isocyanate groups for one hydroxyl group.

The solutions, according to the invention, of adducts of polyisocyanates containing biuret groups with an acetoacetic acid alkyl ester are also excellently suitable for improving lacquer coatings consisting of resins which are in themselves not crosslinked with isocyanates but which contain groups capable of reacting with isocyanates, such as, for example, alkyd resins and polyacrylates. They impart a high gloss, good flexibility and an improved resistance to solvents and weathering to coating films of this type.

The lacquer solutions and coatings produced using the adducts, according to the invention, of polyisocyanate containing biuret groups and an acetoacetic acid alkyl ester can contain pigments and additives which are customary in the lacquer industry.

In Table 1 which follows, synthetic resins 1 to 4 which contain hydroxyl groups and which can be used for stoved coatings, are illustrated by means of examples.

TABLE 1

Composition of the synthetic resins which are to be used with the reaction products, according to the invention, formed from polyisocyanate containing biuret groups and acetoacetic acid alkyl esters, and which were used in accordance with Table 2.

| Synthetic resins | |
|---|---|
| 1 | Copolymer solution consisting of 30.5% by weight of methyl methacrylate, 1.3% by weight of methacrylic acid, 19% by weight of hydroxyethyl methacrylate, 22.8% by weight of 2-ethylhexyl acrylate, 26.4% by weight of butyl methacrylate and 100% by weight of xylene. The viscosity of the solution is Y, measured on the Gardner-Holdt scale. The hydroxyl number has a value of 80 and the acid number is 12. |
| 2 | Epoxide resin based on bisphenol A and epichlorohydrin, having an epoxide equivalent weight of 450-505, described in the leaflet "Beckopox 301" of Messrs. Hoechst AG. |
| 3 | Unplasticised melamine resin, as a 55% strength solution in xylene/butanol, described in the leaflet "Maprenal TTX" of Messrs. Cassella. Density at 20° C.: 1.008. |
| 4 | Castor oil alkyd resin having an oil content of 35% and a phthalic anhydride content of 40%, described in the leaflet "Alftalat AR 351" of Messrs. Hoechst AG. |

EXAMPLE 1

400 g of acetoacetic acid ethyl ester, 67 g of xylene, 67 g of ethylglycol acetate and 1 g of zinc acetylacetonate are heated to 75° C. under nitrogen and whilst stirring and 816 g of a 75% strength by weight solution of a triisocyanate which contains biuret groups and has a NCO content of 16.5–17.0% by weight and has been obtained by reacting 3 mols of hexamethylene diisocyanate and 1 mol of water, are added dropwise uniformly, dissolved in a 1:1 mixture of xylene and ethylglycol acetate, in the course of 2 hours whilst maintaining the temperature of 75° C. and the mixture is kept at 75° C. for 15 hours.

The NCO content is 0.45%, relative to the solvent-free reaction product. The viscosity of the solution is R-S, measured on the Gardner-Holdt scale. The iodine colour number of the solution, measured with the Lovibond 1000 comparator as specified in DIN Specification No. 6,162, is 3–4.

Refractive index of the above solution: $n_D 22 = 1.5170$.

FIG. 1 shows the IR absorption spectrum.

Two mols of hexamethylene diisocyanate are first reacted with one mol of water to form a substituted urea which is then combined with a further mol of hexamethylene diisocyanate to give a biuret:

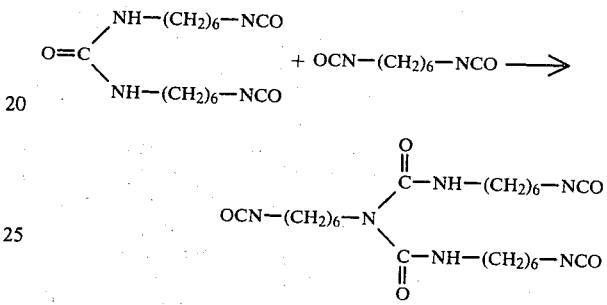

EXAMPLE 2

222 g of acetoacetic acid isopropyl ester, 37.5 g of xylene, 37.5 g of ethylglycol acetate and 0.5 g of zinc acetylacetonate are heated to 95° C. under nitrogen gas and whilst stirring and 408 g of a 75% strength by weight solution of a triisocyanate containing biuret groups, as described in Example 1, are added uniformly dropwise in the course of two hours at the same temperature and the mixture is reacted for 8 hours at 95° C. The NCO content is 0.3%, relative to the solvent-free product. The viscosity of the solution is U, measured on the Gardner-Holdt scale. The iodine colour number of the solution has the value 4. Refractive index of the above solution: $n_D 22 = 1.5022$.

Figure 2:
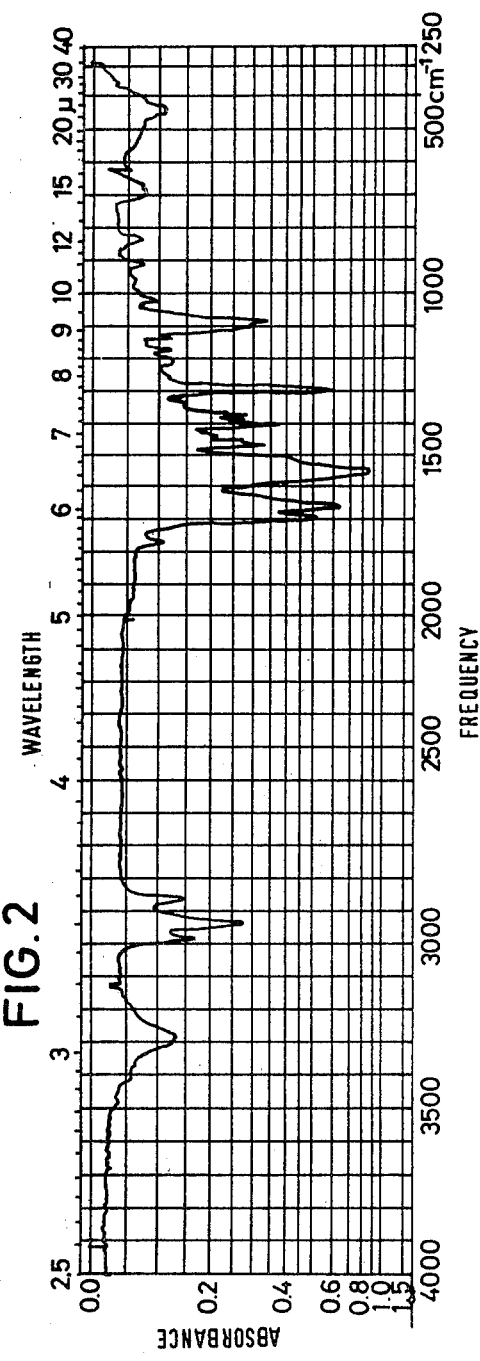

FIG. 2 shows the IR absorption spectrum.

EXAMPLE 3

220 g of acetoacetic acid sec.-butyl ester 37.5 g of xylene, 37.5 g of ethylglycol acetate and 0.5 g of zinc acetylacetonate are heated to 95° C. whilst stirring and admitting nitrogen and 367 g of a 75% strength by weight solution of triisocyanate containing biuret, as described in Example 1, are added uniformly in the course of 2 hours and the reaction is completed in the course of 8 hours at 95° C.

The NCO content is 0.3%, relative to the solvent-free product. The viscosity of the solution is T, measured on the Gardner-Holdt scale. The iodine colour number of the solution has the value 8. Refractive index of the above solution: $n_D 22 = 1.5010$.

Figure 3:
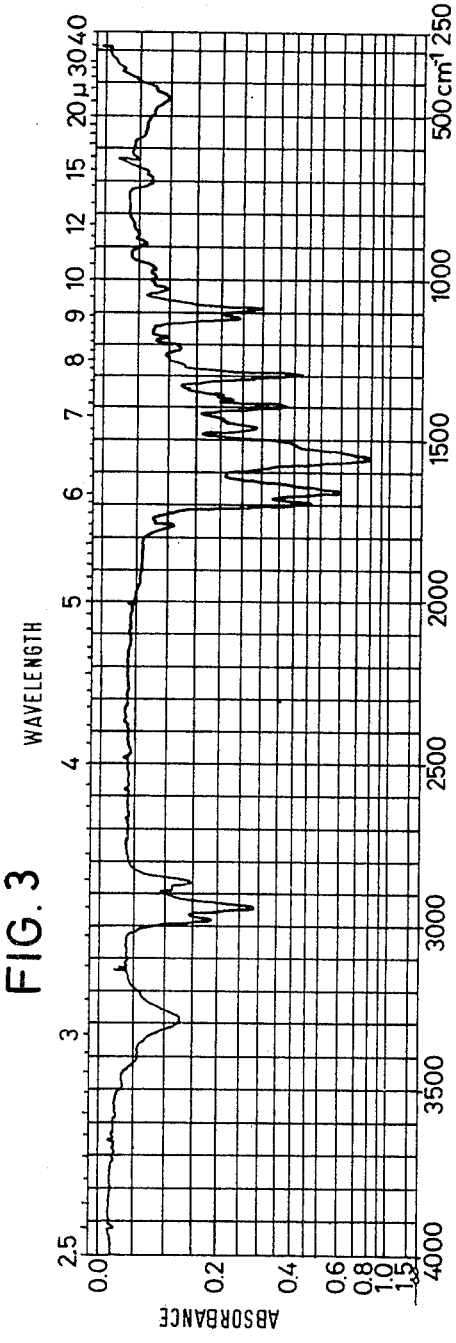

FIG. 3 shows the IR absorption spectrum.

EXAMPLE 4

122 g of acetoacetic acid tert.-butyl ester, 20.5 g of xylene, 20.5 g of ethylglycol acetate and 0.4 g of zinc acetylacetonate are heated to 95° C. under nitrogen gas and whilst stirring and 204 g of a 75% strength by weight solution of a triisocyanate containing biuret, as described in Example 1, are added uniformly dropwise in the course of two hours at the same temperature and the mixture is reacted for 5 hours at 90° C.

The NCO content is 0.8%, relative to the solvent-free product. The viscosity of the solution is V-W, measured on the Gardner-Holdt scale. The iodine colour number of the solution has the value 5. Refractive index of the above solution: $n_D 22 = 1.4980$.

Figure 4:
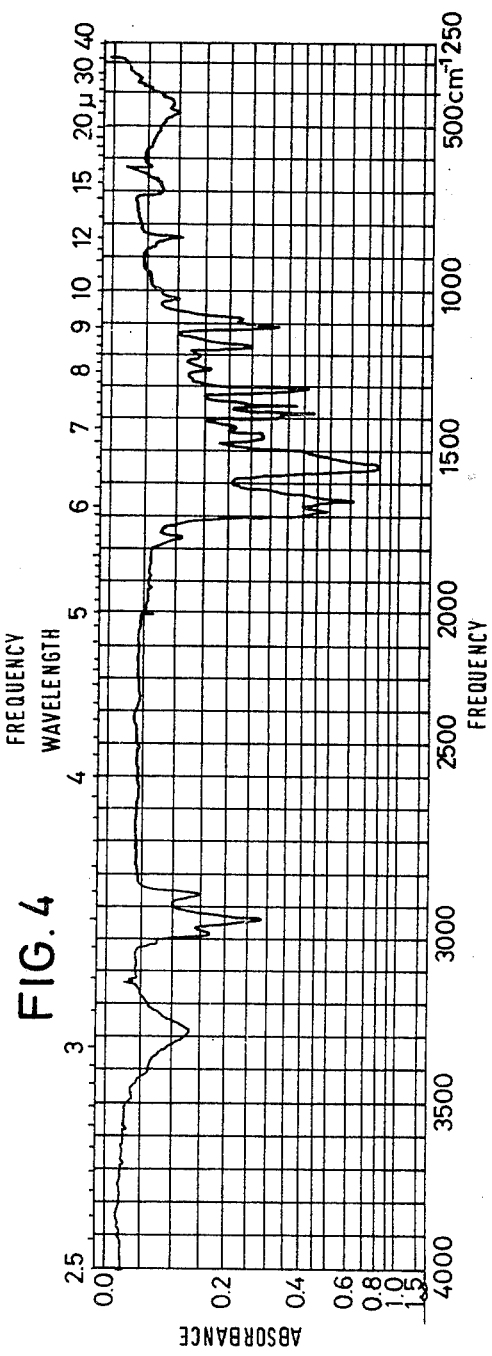

FIG. 4 shows the IR absorption spectrum.

EXAMPLE 5

265 g of acetoacetic acid tert.-amyl ester, 44 g of xylene, 44 g of ethylgycol acetate and 0.5 g of zinc acetylacetonate are heated to 95° C. whilst stirring and admitting nitrogen and 408 g of a 75% strength by weight solution of a triisocyanate containing biuret, as described in Example 1, are added uniformly in the course of 2 hours and the reaction is completed in the course of 4 hours at 90° C.

The NCO content is 0.5%, relative to the solvent-free product. The viscosity of the solution is V-W, measured on the Gardner-Holdt scale. The iodine colour number of the solution reaches the value 8.

Refractive index of the above solution: $n_D 22 = 1.4960$.

Figure 5:
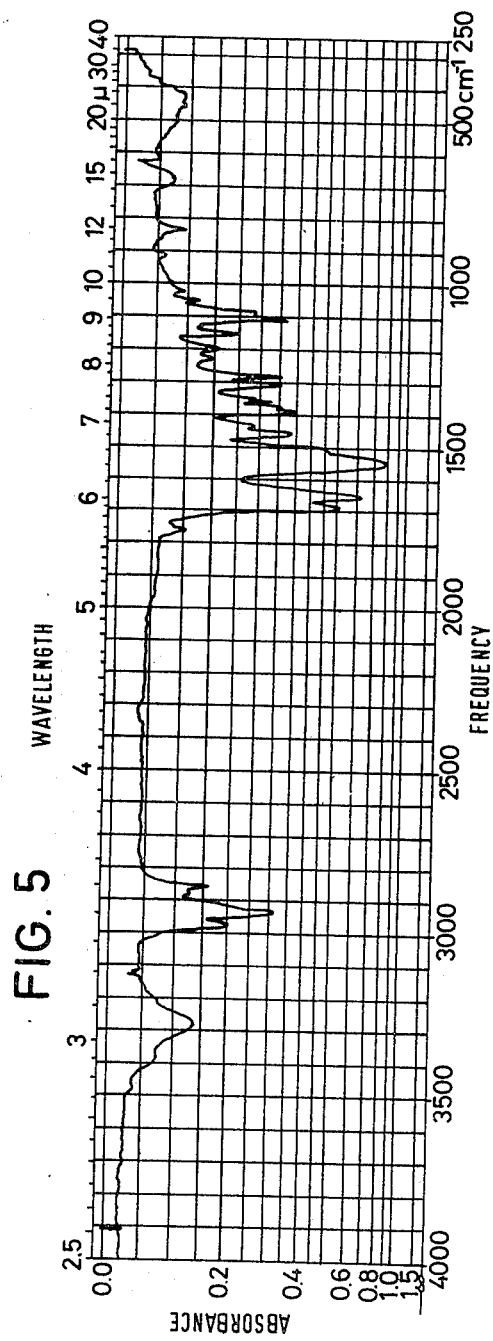

FIG. 5 shows the IR respective spectrum.

As the examples show, the blocked polyisocyanates which contain biuret groups and have been manufactured by the process according to the invention have a NCO content of about 0.2 to 1.0% by weight, after manufacture. Tests by thin layer chromatography have shown that the process products of this invention are free from the diisocyanate which was employed. The NCO content is due to the (mono-masked or di-masked) reaction product.

If the process products are stored at room temperature, the masking advances further, so that after about 2 to 3 weeks after the day of manufacture there is a NCO content of less than 0.1% by weight.

The test results shown in Table 2 were obtained by applying the mixtures, present in solvents, to glass sheets at a dry film layer thickness of 40 to 50 μm.

course of 2 hours and the reaction is completed in the course of 2 hours at 90° to 95° C.

The NCO content is 0.4%, relative to the solvent-free product. The viscosity of the solution is N+, measured on the Gardner-Holdt scale.

The iodine colour number of the solution reaches the value 3 to 4.

Refractive index: $n_D 22 = 1.4982$

Figure 6:
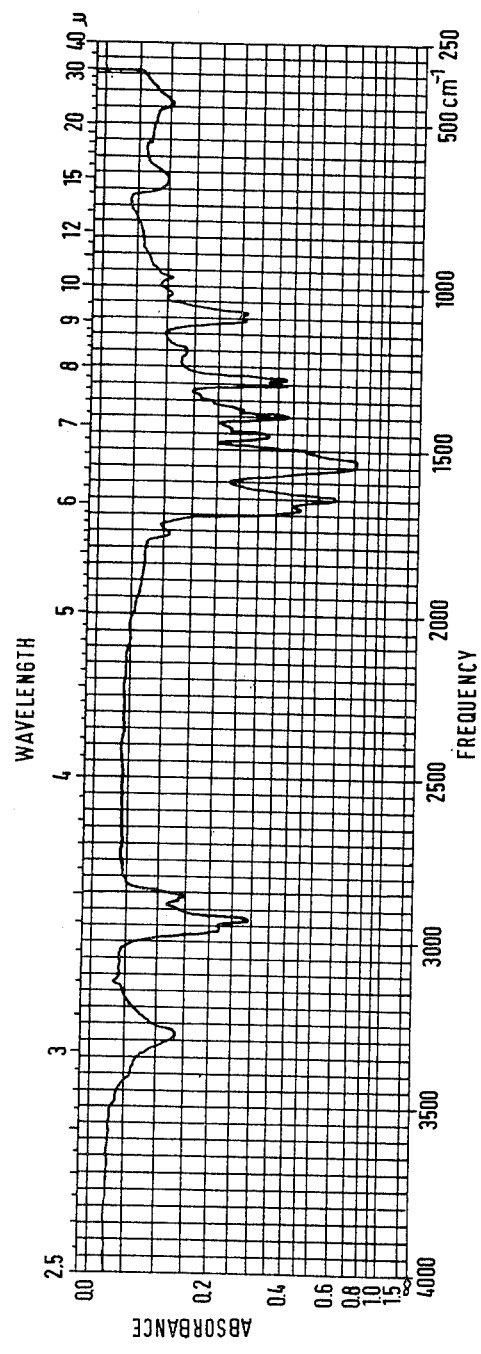

FIG. 6 shows the IR absorption spectrum.

EXAMPLE 7

48.6 g of acetoacetic acid n-butyl ester, 8.1 g of xylene, 8.1 g of ethylglycol acetate and 0.1 g of zinc acetylacetonate are heated to 95° C. under nitrogen gas and whilst stirring and 75.4 g of a 75% strength by weight solution of a triisocyanate containing biuret groups, as described in Example 1, are added uniformly in the course of 2 hours and the reaction is completed in the course of 2 hours at 90° to 95° C.

The NCO content is 0.41%, relative to the solvent-free product. The viscosity of the solution is L—, measured on the Gardner-Holdt scale.

The iodine colour number of the solution reaches the value 3 to 4.

Refractive index: $n_D 22 = 1.4988$.

Figure 7:
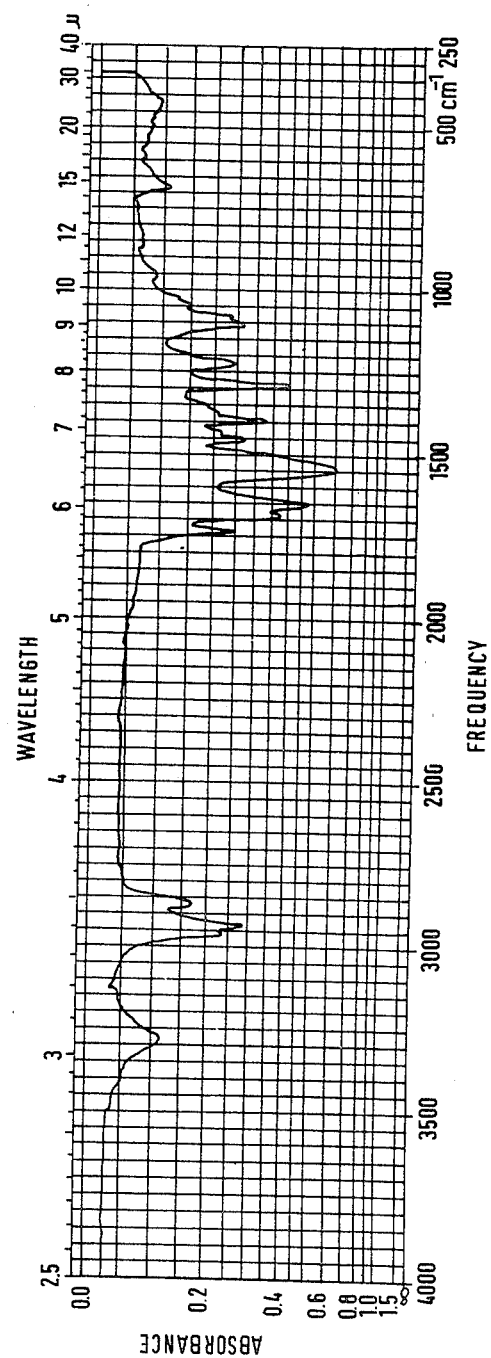

FIG. 7 shows the IR absorption spectrum.

EXAMPLE 8

52.9 g of acetoacetic acid n-amyl ester, 8.8 g of xylene, 8.8 g of ethylglycol acetate and 0.1 g of zinc acetylacetonate are heated to 95° C. under nitrogen gas and whilst stirring and 75.4 g of a 75% strength by weight solution of a triisocyanate containing biuret groups, as described in Example 1, are added uniformly in the course of 2 hours and the reaction is completed in the course of 2 hours at 90° to 95° C.

The NCO content is 0.56%, relative to the solvent-free product. The viscosity of the solution is J+, measured on the Gardner-Holdt scale.

The iodine colour number of the solution reaches the

TABLE 2

Stoved coatings obtained from synthetic resins containing hydroxyl groups and the reaction products, according to the invention, formed from a polyisocyanate containing biuret groups and from acetoacetic acid alkyl esters.

| Synthetic resin used | 1 | 2 | 3 | 4 | 1 | 2 | 3 | 4 |
|---|---|---|---|---|---|---|---|---|
| | 80% by weight | 70% by weight | 70% by weight | 80% by weight | 80% by weight | 70% by weight | 70% by weight | 80% by weight |
| Example 1 according to the invention | 20% by weight | 30% by weight | 30% by weight | 20% by weight | | | | |
| Example 4 according to the invention | | | | | 20% by weight | 30% by weight | 30% by weight | 20% by weight |
| Stoving temperature | | 130° C. | | 30 minutes | | 100° C. | 30 minutes | |
| Dry film layer thickness in μm | 45 | 50 | 45 | 50 | 45 | 45 | 45 | 50 |
| Film compatibility | 1 | 1 | 1 | 1 | 1 | 1 | 1 | 1 |
| Yellowing | 1 | 1 | 1 | 1-2 | 1 | 2 | 2 | 1 |
| Elasticity | 1-2 | 2 | 2 | 1 | 1-2 | 2 | 2 | 1 |
| Resistance to xylene after 10 minutes | 2 | 2 | 1 | 3 | 2 | 2 | 1 | 3 |
| Pendulum hardness by Konig's method in seconds | 140 | 220 | 180 | 80 | 135 | 205 | 160 | 80 |

EXAMPLE 6

48.6 g of acetoacetic acid isobutyl ester, 8.1 g of xylene, 8.1 g of ethylglycol acetate and 0.1 g of zinc acetylacetonate are heated to 95° C. under nitrogen gas and whilst stirring and 75.4 g of a 75% strength by weight solution of a triisocyanate containing biuret groups, as described in Example 1, are added uniformly in the value 4.

Refractive index: $n_D 22 = 1.4969$.

Figure 8:
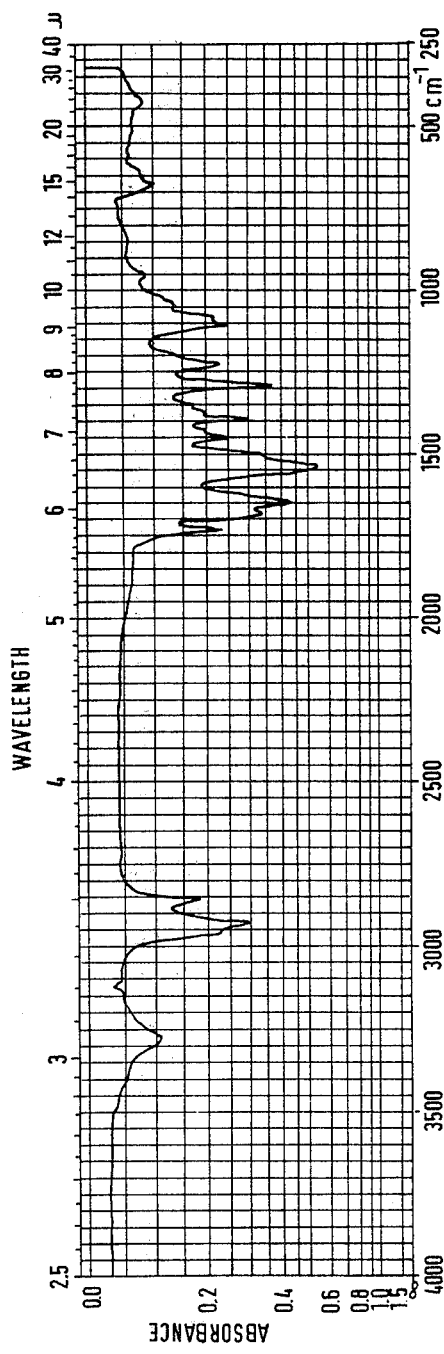

FIG. 8 shows the IR absorption spectrum.

EXAMPLE 9

35.7 g of acetoacetic acid methyl ester, 5.9 g of xylene, 5.9 g of ethylglycol acetate and 0.1 g of zinc acetylacetonate are heated to 95° C. under nitrogen gas and whilst stirring and 75.4 g of a 75% strength by weight solution of a triisocyanate containing biuret groups, as described in Example 1, are added uniformly in the course of 2 hours and the reaction is completed in the course of 2 hours at 90° to 95° C.

The NCO content is 0.49%, relative to the solvent-free product. The viscosity of the solution is U, measured on the Gardner-Holdt scale.

The iodine colour number of the solution reaches the value 9.

Refractive index: $n_D 22 = 1.5064$

Figure 9:
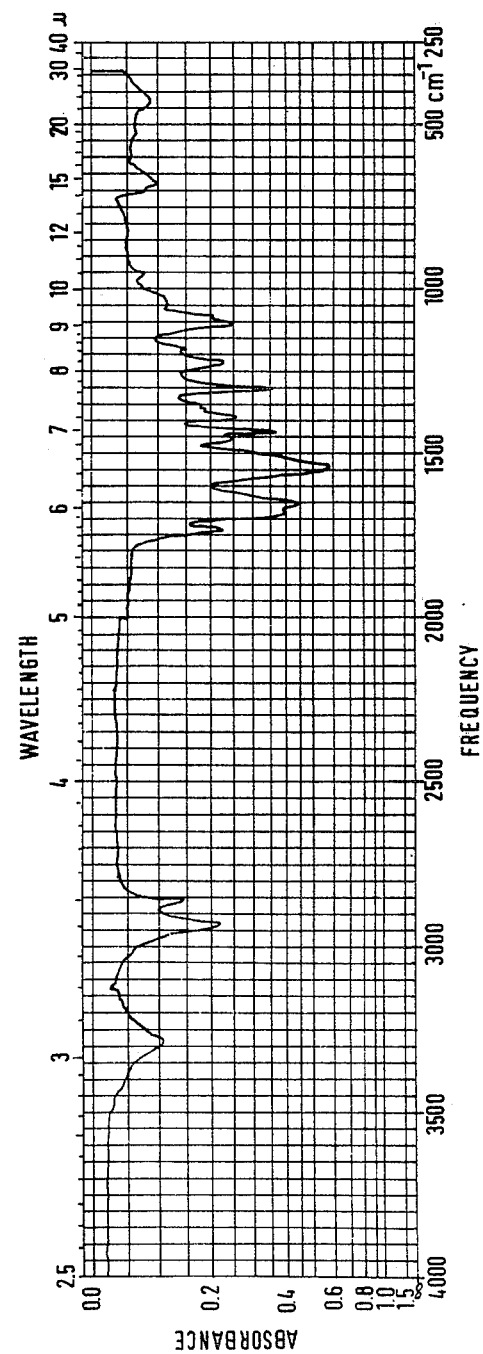

FIG. 9 shows the IR absorption spectrum.

EXAMPLE 10

Reaction of the triisocyanate in a first stage with acetoacetic acid ethyl ester to give a product of the formula Ia and further reaction with acetoacetic acid tert.-butyl ester to give a completely masked product of the formula Ic. 1st stage 19.5 g of acetoacetic acid ethyl ester (0.15 mol), 3.2 g of xylene, 3.2 g of ethylglycol acetate and 0.1 g of zinc acetylacetonate are heated to 95° C. under nitrogen gas and whilst stirring and 75.7 g of 75% strength by weight solution of a triisocyanate (0.1 mol) containing biuret groups, as described in Example 1, are added in the course of 2 hours and the reaction is completed in the course of 2 hours at 90°-95° C.

The NCO content is 12.6%, relative to the solvent-free product.

2nd stage 29.8 g of a mixture consisting of 23.7 g of acetoacetic acid tert.-butyl ester (0.15 mol), 4 g of xylene and 4 g of ethylglycol acetate is added to 96 g of the solution of the reaction product from the 1st stage and the mixture is heated to 95° C. and is reacted for a further 2 hours at this temperature. The NCO content is 0.5%, relative to the solvent-free product. The viscosity of the solution at 25° C. is U-V, measured on the Gardner-Holdt scale. The iodine colour number has the value 10. The refractive index $n_D 22$ has the value 1.4998.

EXAMPLE 11

Preparation of a completely masked product having the formula (Ic) in xylene using zinc acetylacetonate as the catalyst.

40 g of acetoacetic acid ethyl ester and 0.1 g of zinc acetylacetonate are heated to 95° C. and 79.5 g of a 75% strength by weight solution in xylene of a triisocyanate which contains biuret groups and has a NCO content of 16.0% by weight and has been obtained by reacting three mols of hexamethylene diisocyanate and 1 mol of water, are added uniformly, dropwise, in the course of two hours whilst maintaining a temperature of 95° C. and the mixture is reacted for four hours at 95° C. The NCO content is 0.3%, relative to the solvent-free product. The viscosity at 23° C. is T, measured on the Gardner-Holdt scale. The iodine colour number of the solution, measured with the Lovibond 1000 comparator in accordance with DIN Specification 6162, is 5. The product is a liquid with a faint lemon-yellow colour.

If this xylene solution is diluted to 20% strength by weight solutions with the following solvents: ethyl acetate, toluene, xylene or benzene, clear solutions which exhibit no sediment are obtained.

As the comparison tests show, the blocked polyisocyanates manufactured according to the invention from a triisocyanate containing biuret groups and from acetoacetic acid alkyl esters exhibit a better solubility than that of the known reaction products, when diluted with xylene, ethyl acetate, toluene and benzene.

Comparison Tests to Demonstrate the Technical Advance Achieved

Preparation of a completely masked product having the formula (Ic) in xylene using sodium as the catalyst according to DT-OS 2,342,603.

40 g of acetoacetic acid ethyl ester and 0.17 g of sodium are heated to 95° C. and 79.5 g of a 75% strength by weight solution in xylene of a triisocyanate containing biuret groups are reacted therewith in the same manner as described in Example 11.

The product was a dark brown to reddish liquid which in some cases deposited crystals which had to be filtered off. The viscosity of the solution at 23° C. is W-X, measured on the Gardner-Holdt scale. The iodine colour number of the solution, measured with the Lovibond 1000 comparator in accordance with DIN Specification No. 6162, was 150.

When this xylene solution is diluted to 20% strength by weight solutions with the following solvents: ethyl acetate, toluene, xylene or benzene, insoluble sediments separate out. The proportion is about 4 to 6% by weight, relative to the dissolved reaction product formed from the triisocyanate containing biuret groups and from acetoacetic acid ethyl ester.

EXAMPLE 12

Partially blocked polyisocyanates formed from a triisocyanate containing biuret groups and from acetoacetic acid alkyl esters.

3.8 g of xylene, 3.8 g of ethylglycol acetate, 150.8 g (0.2 mol) of a 75% strength by weight solution of a triisocyanate containing biuret groups, as described in Example 1, and 0.13 g of zinc acetylacetonate are heated to 75° C. in a flask equipped with a stirrer and a reflux condenser and 23.8 g (0.2 mol) of acetoacetic acid methyl ester are added dropwise in the course of two hours at the same temperature. A NCO content of 12.8%, relative to the solvent-free product, is obtained after a reaction time of four hours. The viscosity of the solution at 25° C. is P, measured on the Gardner-Holdt scale. The iodine colour number has the value 5. The refractive index at 22° C. is 1.4962.

The further Examples, 13 to 17, are carried out in the same way as described in Example 12 (see Table 3 which follows).

TABLE 3

Partially blocked polyisocyanates formed from a triisocyanate containing biuret groups and from acetoacetic acid alkyl esters.

| Example | Triisocyanate 0.2 mol | Acetoacetic acid alkyl ester 0.2 mol | Catalyst zinc acetylacetonate | NCO content after the reaction in %++ | Iodine colour number | Viscosity of the solution+ | Refractive index at 22° C. |
|---|---|---|---|---|---|---|---|

TABLE 3-continued

Partially blocked polyisocyanates formed from a triisocyanate containing biuret groups and from acetoacetic acid alkyl esters.

| | | | | NCO content after the reaction in %++ | Iodine colour number | Viscosity of the solution+ | Refractive index at 22° C. |
|---|---|---|---|---|---|---|---|
| 13 | 150.8 g | 26 g of acetoacetic acid ethyl ester | 0.14 g | 12.2 | 4 | K | 1.4950 |
| 14 | 150.8 g | 31.6 g of acetoacetic acid tert.-butyl ester | 0.15 g | 9.8 | 4 | X-Y | 1.4970 |
| | Triisocyanate 0.2 mol | Acetoacetic acid alkyl ester 0.4 mol | Catalyst zinc acetylacetonate | NCO content after the reaction in %++ | Iodine colour number | Viscosity of the solution+ | Refractive index at 22° C. |
| 15 | 150.8 g | 46.4 g of acetoacetic acid methyl ester | 0.16 g | 5.2 | 5 | T | 1.5013 |
| 16 | 150.8 g | 63.2 g of acetoacetic acid tert.-butyl ester | 0.18 g | 3.9 | 4 | Y-Z | 1.4989 |
| 17 | 150.8 g | 52 g of acetoacetic acid ethyl ester | 0.17 g | 4.9 | 4 | T+ | 1.5015 |

+measured at 25° C. on the Gardner-Holdt scale
++relative to the solvent-free product

I claim:

1. Process for the manufacture of a completely or partially blocked compound having the formula

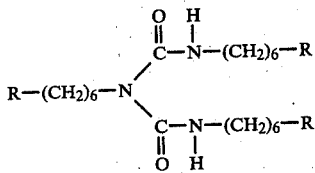

(I)

wherein R denotes the radical

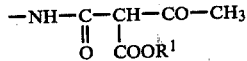

and one to three units of R are present in the compound and wherein, in the case wherein one or two units of R having this meaning are present, the remaining radical R denotes the radical —NCO, and wherein $R^1$ denotes the methyl, ethyl, propyl, isopropyl, n-butyl, tert.-butyl, isobutyl, sec.-butyl, pentyl, hexyl, heptyl, octyl, nonyl, decyl or dodecyl radical, characterized in that an acetoacetic acid alkyl ester in which the alkyl radical consists of the methyl, ethyl, propyl, isopropyl, n-butyl, tert.-butyl, isobutyl, sec.-butyl, pentyl, hexyl, heptyl, octyl, nonyl, decyl, or dodecyl, is reacted, by warming, in the presence of zinc acetoacetonate as catalyst, with an about 75 percent strength by weight solution of a triisocyanate containing biuret groups having an NCO content of 16.5 to 17.0 percent by weight and which triisocyanate has been obtained by reacting three moles of hexamethylene diisocyanate with one mol of water, and for every NCO group to be blocked in the ratio of acetoacetic acid ester: NCO of 1 to 1.1:1, to obtain a compound of formula I.

* * * * *

UNITED STATES PATENT AND TRADEMARK OFFICE
CERTIFICATE OF CORRECTION

PATENT NO. : 4,332,965

DATED : June 1, 1982

INVENTOR(S) : Horst Dalibor

It is certified that error appears in the above—identified patent and that said Letters Patent is hereby corrected as shown below:

Col. 2, line 41; insert after "propyl,", -- isopropyl, --
Col. 4, lines 5 & 6; "($CH_2$-)$_3$-" the formula is incorrectly hyphenated and should read -- $(CH_2)_3$- --
Col. 4, lines 8 & 9; "-$CH_2$-$CH_3$;" the formula is incorrectly hyphenated and should read -- -$CH_2$-$CH_3$; --
Col. 4, line 14; "of" should read -- to --
Col. 6, line 28; "aids" should read -- acids --
Col. 9, line 12; "ethylgycol" should read -- ethylglycol --
Col. 9, line 24; replace "respective" with -- absorption --
Col. 9, TABLE 2, second to the last line; "Konig's" should read -- König's --
Col. 11, line 28; "of 75%" should read -- of a 75% --

Signed and Sealed this

Twenty-first Day of September 1982

[SEAL]

Attest:

Attesting Officer

GERALD J. MOSSINGHOFF

Commissioner of Patents and Trademarks